(12) United States Patent
Laffafian et al.

(10) Patent No.: US 6,479,288 B1
(45) Date of Patent: Nov. 12, 2002

(54) METHOD AND APPARATUS FOR INTRODUCING SUBSTANCES INTO THE CELL PLASMA MEMBRANE AND/OR CYTOSOL

(75) Inventors: Iraj Laffafian; Maurice Bartlett Hallett, both of Cardiff (GB)

(73) Assignee: University of Wales College of Medicine, Cardiff (GB)

( * ) Notice: Subject to any disclaimer, the term of this patent is extended or adjusted under 35 U.S.C. 154(b) by 0 days.

(21) Appl. No.: 09/622,412

(22) PCT Filed: Feb. 16, 1999

(86) PCT No.: PCT/GB99/00475

§ 371 (c)(1),
(2), (4) Date: Aug. 16, 2000

(87) PCT Pub. No.: WO99/41401

PCT Pub. Date: Aug. 19, 1999

(30) Foreign Application Priority Data

Feb. 17, 1998 (GB) ............................................... 9803214
Sep. 26, 1998 (GB) ............................................... 9820930

(51) Int. Cl.[7] ........................... C12N 15/89; C12M 3/00
(52) U.S. Cl. ..................... 435/455; 435/468; 435/285.1
(58) Field of Search ................................ 435/455, 468, 435/285.1

(56) References Cited

U.S. PATENT DOCUMENTS 5,457,041 A * 10/1995 Ginaven et al. ......... 435/172.1

FOREIGN PATENT DOCUMENTS

| DE | 196 29 143 | 1/1998 |
| FR | 2 754 272 | 4/1998 |
| GB | 2 193 326 | 2/1999 |

* cited by examiner

Primary Examiner—Terry McKelvey
(74) Attorney, Agent, or Firm—Young & Thompson

(57) ABSTRACT

There is disclosed a method for introducing agents into the cytosol and/or plasma membrane of a cell. The method comprises the steps of: (a) coating at least a portion of a tip of a transferring means with a lipid; (b) bringing the lipid-coated tip of the transferring means into contact with the cell; and (c) transferring the contents of the transferring means into the cytosol and/or plasma membrane of the cell without entering the cytoplasm. Also disclosed is a transferring means for injecting agents into the cytosol and/or plasma membrane of the cell and a method of coating a tip of a transferring means with a lipid. A suitable packaging and a method for preparing the transferring means for use are also disclosed.

25 Claims, 4 Drawing Sheets

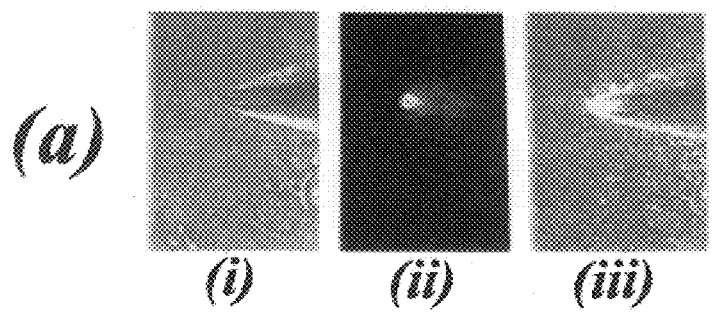
(a)
(i) (ii) (iii)
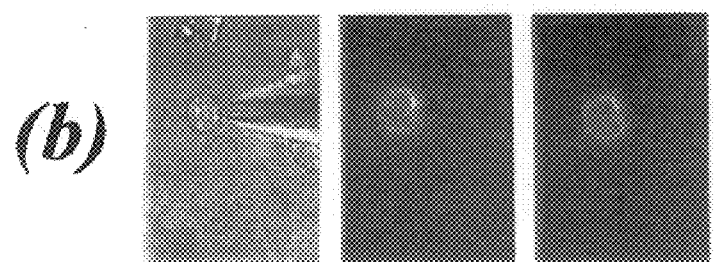
(b)
(i) (ii) (iii)
*Fig. 1*
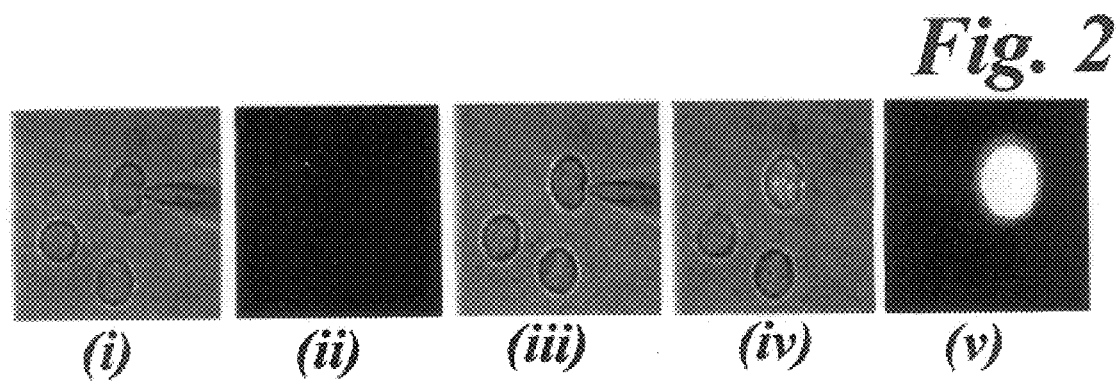
(i) (ii) (iii) (iv) (v)
*Fig. 2*
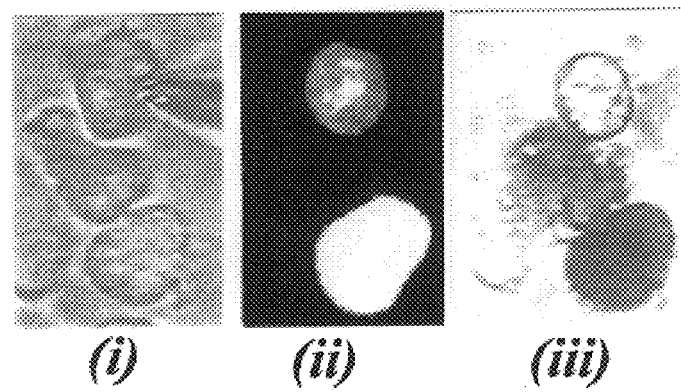
(i) (ii) (iii)
*Fig. 3*

METHOD AND APPARATUS FOR INTRODUCING SUBSTANCES INTO THE CELL PLASMA MEMBRANE AND/OR CYTOSOL

This invention relates to a method for introducing an agent into the cytosol or plasma membrane of a cell using a lipid-coated tip of a pipette or rod or the like to contact, but not penetrate, the cell. In addition, the invention relates to a pipette or rod having a lipid-coated tip for introducing agents into the cytosol or plasma membrane of a cell and also to a method of coating a tip of a pipette or rod with the lipid.

The micro-injection of agents such as proteins and nucleic acid (mRNA and DNA) into the cytosol of living cells is a powerful technique which has led to many new discoveries. Furthermore, it underlies some new approaches to molecular and genetic engineering and is becoming useful in in vitro fertilisation. However, micro-injection by the insertion of a glass micro-pipette into the cell is a potentially damaging event and is limited, at present, to cells which are both large and robust. Micro-injection of small mammalian cells (spherical diameter =2–15 $\mu$m) or very flat cells (1–2 $\mu$m thickness) has always been difficult to achieve without damaging the cell and resulting in poor cell survival. The penetration of small cells, especially spherical cells, requires a rapid entry and exit "stab", as slow withdrawal of the micropipette often results in breaking the cell. Thus "stab injection", where the micro-injector is within the cell for approximately 100 msec, high pressure (100–200 mbar) has to be used to introduce sufficient material into the cell during that time. This must be carefully controlled as insufficient pressure results in too little material being injected and excessive pressure causes cell damage or rupture. The cell must also be firmly attached to a substrate for the "stab" to effectively penetrate the cell membrane. Apart from these problems, the process is essentially blind and, because of the small size of the cell and the large volume of the cell cytoplasm occurred by organelles such as the nucleus, lysosomes and ER, insertion of the micro-injector at high speed is likely to cause intracellular damage. For example, the micro-pipette entering the cell with a velocity of approximately 700 $\mu$m/sec is likely to displace, damage or enter the nucleus (which in small cells such as neutrophils and basophils accounts for up to 50% of the cell volume) rather than enter directly into the cytosol even if the plasma membrane survives.

Traditional pressure injection has been successfully used in a number of cell-types, including, hepatocytes (Cobbold) and Jurkat cells. However, the success rate is limited, with many cells failing to survive stab injection. There have been various attempts to minimise the problem of cell damage, including the use of pharmacological $Ca^{2+}$ channel blockers. Other techniques have also been used for introducing agents, such as peptide inhibitors, antibodies etc into cells, by membrane permeabilisation using chemical or biological molecules, or techniques such as by electroporation. While this approach can be useful, cell damage is great, and mechanisms by which the cell repairs the damage are poorly understood, but which may involve $Ca^{2+}$ and active signalling by the cell. Thus the recovered cells may not represent those in a state that was originally intended for study. Another method which has been used is internal perfusion. In this technique, the micro-pipette does not enter the cell, but membrane is sucked into the mouth of the micro-pipette causing a local rupture of the cell membrane at that point. This minimises damage to intracellular structures, but the process of "breaking into" the cell results in an irreversible seal and the cell must remain attached to the pipette for its survival. This precludes studies of cell shape change etc, and the negative pressure required to break-in also withdraws cytosol if not carefully controlled. In any case, during the period that the micro-pipette is attached diffusion of material both from the micro-pipette into the cell and from the cytosol into the micro-pipette occurs. Diffusion out of the cell of important small molecules such as GTP, ATP etc essentially limits the usefulness of this technique to those processes in which they are not involved or are regulated by the contents of the micro-pipette. All these techniques, while useful, thus have limitations.

Other approaches which do not involve glass micro-injection have also been used. One early approach was the use of lipid fusion, either by the use of liposomes or erythrocyte ghost function. While lipid fusion can be successful for introducing cDNA etc into cells as with lipofection, the amount of material injected is very small and perhaps only one copy of the cDNA is sufficient for the experiment. For example to inject a small cell (d=10 $\mu$m) with 1% of its volume by fusion of liposomes (d=50 nm) requires thousands of fusion events. This number of fusion events is unlikely and the use of liposomes for cell physiology has not been widely successful. Fusion of larger vesicles such as red cell ghosts has also been used, where one fusion event can introduce a large amount of material. However, a large amount of foreign membrane is also introduced and the cells are essentially hybrids rather than original cells.

According to a first aspect of the present invention, there is provided a method for introducing an agent in to the cytosol and/or plasma membrane of a cell, comprising the steps of:
  (a) coating at least a portion of a tip of a transferring apparatus with a lipid;
  (b) bringing the lipid-coated tip of the transferring apparatus into contact with the cell; and
  (c) transferring at least some of the contents of the transferring apparatus into the cytosol and/or plasma membrane of the cell without entering the cytoplasm.

The transferring apparatus is preferably a pipette or rod. The pipette is usually a micro-pipette (usually manufactured of glass) and the rod is usually a micro-rod. The micro-rod is a device (usually made of glass) which is solid and has no internal bore. A micro-pipette may be used for lipid-assisted micro-injection of substances into the cytosol or into the plasma membrane, whereas a micro-rod may be used to introduce substances exclusively into the plasma membrane. The micro-rod has the advantage that lipids and lipid-soluble molecules such as proteins can be transferred from the micro-rod to the cell and vice versa without aqueous transfer into the cytosol. In the case of a rod, the "contents" of the transferring apparatus may be present in the lipid on the tip.

It has been found that the technique provides fusion between the lipid at the tip and the cell membrane which results in a channel into the cell cytosol, without the possibility of intracellular organelle damage, and low pressure in the transferring apparatus ensures that the amount of material injected is controlled and does not unduly damage the cell. Furthermore, as only contact, rather than penetration, is required for agent introduction with this approach, the cell need not be firmly adherent. The applicants have carried out the use of simple lipid assisted micro-injection ("SLAM") on human neutrophils, when loosely adherent as spherical individual cells or spread on glass coverslips with a cell thickness of just 1–3 $\mu$m. These cells have been very difficult, if not impossible, to undergo successful microinjection by conventional means.

Preferably, at least some of the contents of the transferring apparatus are transferred under pressure, which pressure is small enough to prevent damage to the cell contents. This pressure may typically be in the range of between 5 and 40 mbar.

The method is particularly useful when the cell is a living cell which remains living after transferring the contents of the transferring apparatus into the cytosol and/or plasma membrane of the cell. For example, the cell may be a small mammalian cell. Thus, the method of the invention has particular use in introducing agents in to a cell having a spherical diameter of between 2 and 15 $\mu$m, or a cell of substantially flat form having a thickness of only 1 to 3 $\mu$m. Thus, the cell may typically be a human neutrophil cell, having a thickness of 1 to 3 $\mu$m.

Typically, transfer of the lipid and lipid-soluble molecules takes place between the transferring apparatus and the cytosol and/or plasma membrane of the cell when the contents of the transferring apparatus are transferred to the cell. The contents of the transferring apparatus are preferably in the form of an aqueous solution which may include a dye, for example lucifer yellow, which may aid in investigating transfer of the aqueous contents into the cell.

The method may further comprise the step of swelling the lipid to form a lipid-coating or bi-molecular layer (bilayer) prior to bringing the tip into contact with the cell.

In the present context, a lipid is any substance of a fat-like nature. Thus, the expression includes fatty acids or derivatives, which are soluble in organic solvents and insoluble in water, for example the simple fats and waxes and the phospholipids and cerebrosides. The expression also includes such compounds as sterols and squalene. As examples, both natural and synthetic lipids, and phospholipids, could be used in the present invention. The lipid preferably comprises phosphatidylcholine-oleyl-palmitoyl (PCOP). The PCOP may be dissolved in any suitable solvent, for example chloroform, before application of the lipid to the transferring apparatus, prior to drying of the lipid.

According to a second aspect of the present invention, there is provided a transferring apparatus for introducing an agent into the cytosol and/or plasma membrane of a cell, comprising a lipid-coated tip capable of transferring at least some of the contents of the transferring apparatus to the cell without entering the cytoplasm.

As discussed above, the transferring apparatus may be a pipette or a rod.

The tip may be disposable. Thus, there may be provided a lipid-coated tip for use in the transferring apparatus.

According to a further aspect of the present invention, there is provided a kit for introducing an agent into a cell, the kit comprising an agent and a transferring apparatus for introducing the agent into the cytosol and/or plasma membrane of a cell, wherein the apparatus comprises a lipid-coated tip capable of transferring at least some of the contents of the apparatus into the cytosol and/or plasma membrane of the cell without entering the cytoplasm.

According to a further aspect of the present invention, there is provided a method of transfecting a cell, which comprises introducing into the cell a transfection agent, the method comprising the steps of:

(a) coating at least a portion of a tip of a transferring apparatus with a lipid;

(b) bringing the lipid-coated tip of the transferring apparatus into contact with the cell; and (c) transferring at least some of the contents of the transferring apparatus to the cell. There is also provided a cell or product of a cell treated in accordance with the methods of the invention.

According to a further aspect of the present invention, there is provided a method of coating a tip of a transferring apparatus with a lipid, comprising applying a lipid solution to the tip of the transferring apparatus and evaporating the solvent from the lipid solution.

The method is particularly suitable for the mass production of lipid coated pipettes or rods. The solvent is preferably volatile. The contact of the transferring apparatus with the lipid solution can be achieved in any suitable way, examples being immersion in solutions of the lipid or by passage of the transferring apparatus through an aerosol spray of the lipid solution.

The lipid solution may, in one embodiment, be provided in an air-tight and light-tight container.

The method of coating the tip may further comprise the step of loading the transferring apparatus with an aqueous solution prior to applying the lipid solution. The method may further comprise the step of, placing the transferring apparatus in an aqueous solution such that the dried lipid swells to form a lipid-coating or bi-molecular layer.

According to a further aspect of the present invention, there is provided a packaging for a transferring apparatus having a lipid coated tip, the packaging comprising an air-tight sheath member for receiving the transferring apparatus, wherein, when the packaging is in use, the sheath member surrounds at least the lipid-coated tip such that preservation of the lipid in its molecular form is maximised.

The packaging preferably further comprises an outer packaging member. The packaging may additionally further comprise a water-absorbing agent within the outer packaging member, for example silica gel. Preferably, the outer packaging member is flushed with an inert gas, for example nitrogen, before sealing thereof.

According to a further aspect of the present invention, there is provided a method of preparing a lipid-coated tip of a transferring apparatus, comprising:

(a) positioning a tip of a transferring apparatus in a sheath having an aperture therein;

(b) immersing the tip in a lipid in a solvent thereby allowing the solvent to pass through the aperture; and (c) evaporating the solvent.

The aperture may be positioned in a base and side wall of the sheath, which is preferably removable.

According to a further aspect of the present invention, there is provided a method of preparing a transferring apparatus having a lipid-coated tip for use in introducing an agent in to the cytosol and/or plasma membrane of a cell, the method comprising the steps of:

a) placing the substance to be introduced in to the transferring apparatus;

b) immersing the tip of the transferring apparatus in an aqueous liquid surrounding the cell; and c) applying a pressure to the contents of the transferring apparatus.

Preferably the substance to be introduced is placed in to the transferring apparatus from the rear (i.e. the non-lipid-coated end). A bi-molecular lipid layer may form on the transferring apparatus as it is immersed in the aqueous liquid. In step c), preferably a high pressure is applied, which may be between 1000 and 3000 millibar. The pressure is preferably applied transiently (eg. 0.1 to 2 secs). When the application of the pressure is stopped, the lipid at the tip reforms and the transferring apparatus is ready for use in lipid assisted micro-injection techniques as described.

Whilst the invention has been described above it extends to any inventive combination of the features set out above or in the following description.

The invention will now be described, by way of example, with reference to the accompanying drawings and example, and in which:

BRIEF DESCRIPTION OF THE DRAWINGS

FIGS. 1(a) (i) to (iii) and (b) (i) to (iii) are images showing lipid transfer from a micro-pipette to a cell membrane;

FIGS. 2(i) to (v) are images showing transfer of aqueous contents to the cytosol;

FIGS. 3(i) to (iii) are images showing cell damage associated with injection pressure;

FIG. 6(i) shows a packaging for apparatus of the invention;

EXAMPLE

Materials

Figure 4:
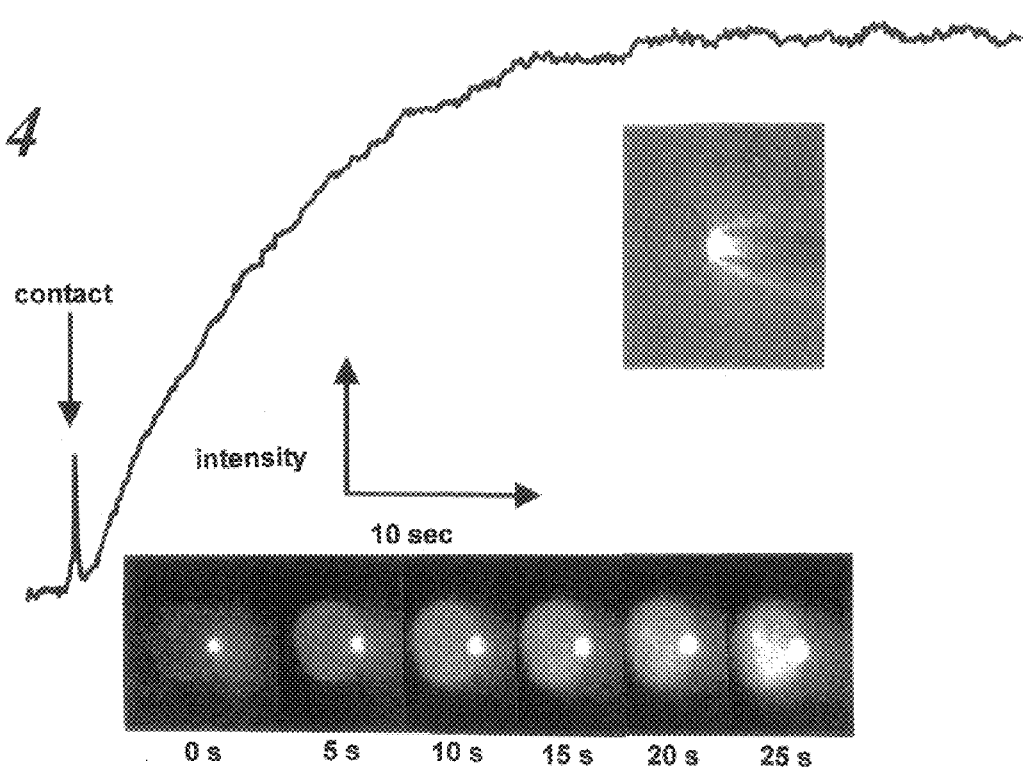
FIG. 4 is a graph showing the time course of transfer of material to the cytosol.

Micro-pipettes were pre-made (Eppendorf) and the micro-manipulation achieved using Eppendorf manipulator (model 9525). Phosphatidylcholine-oleyl-palmitoyl, PCOP, (Sigma) was dissolved in chloroform (20 mg/ml) and stored below 0° C. Aliquots of this solution were diluted 1/30 with chloroform before use (final PCOP concentration approximately 1 mM). $DiIC_{18}(3)$ (1, 1'-dioctadecyl-3,3,3'.3'-tetramethylindocarbo-cyanine perchlorate) was obtained from Molecular Probes, Oregon. Lucifer yellow CH was dissolved in water to a concentration of 10–50 mg/ml for use.

Neutrophil Isolation

Neutrophils were isolated from heparinized blood of healthy volunteers as is known in the art. Following dextran sedimentation, centrifugation through Ficoll-Paque (Pharmacia) and hypotonic lysis of red cells, neutrophils were washed and resuspended in Krebs buffer (120 mM NaCl, 4.8 mM KCl, 1.2 mM $KH_2PO_4$, 1.2 mM $MgSO_4$, 1.3 mM $CaCl_2$, 25 mM HEPES (N-[2-hydroxyethyl} piperazine —N'-[2-ethanesulfonic acid] and 0.1% bovine serum albumin, adjusted to pH 7.4 with NaOH).

Lipid coating of micro-pipette

The micro-pipette was back loaded with sufficient aqueous volume of lucifer yellow solution so that it exerted a pressure which just off-set the capillary pressure when the micro-pipette was placed near the cell. The micro-pipette was then connected to a control pressure device (Ependorf, micro-injector) with the pressure set to zero, and a drop (approx 10 µl) of lipid solution (PCOP dissolved in chloroform (1 mM) kept on ice was applied to the tip of the micro-pipette. Evaporation of the chloroform resulted in a coating of lipid on the glass. The micro-pipette was then placed in the aqueous medium bathing the cells, and the dried lipid on the tip of the micro-pipette swollen to form a bilayer. The pressure in the micro-pipette was increased to 10 mbar and the lack of ejection or diffusion of the dye from the micro-pipette observed by epi-fluorescence was taken as evidence that an effective lipid seal had formed at the micro-pipette tip.

The "SLAM" procedure

Neutrophils were allowed to sediment onto a glass coverslips which were mounted for viewing with an oil immersion objective (100×). The loaded lipid-coated micro-pipette was brought into the field of view using a motorised microprocessor controlled micro-manipulator and brought in gentle contact with the surface of a neutrophil. This resulted in the transfer to the cell of both the lipid and the aqueous contents of the micro-pipette to the cell. The pressure within the micro-pipette was regulated and held low (5–mbar) as this reduced cell damage.

Image Collection and Analysis

Images were acquired using either a low sensity CCD camera or, for low level fluorescence detection, an intensified CCD camera (ISIS, Photonics, UK) coupled to an inverted Zeiss IM35 microscope. Images were subsequently recorded from tape using a video printer (Mitsubishi). The intensity of signals from individual cells was quantified by setting an exclusion mask over the cell of interest for photometric recording using a photomultiplier tube set to 100 msec integration time for acquisition using Spex DM3000CM software.

The results of the methods were obtained as follows (i) Lipid transfer

In order to demonstrate the coating of the tip of the micro-pipette with lipid, as described in the methods, the fluorochrome$DiIC_{18}(3)$ (1,1'-dioctadecyl-3,3,3'.3'-tetrameth-ylindocarbo-cyanine perchlorate) was used. This probe is weakly fluorescent in water but fluoresces strongly in lipid bilayers and was thus used to visualise the lipid coating at the micro-pipette tip (FIG. 1). This demonstrated that the procedure described above resulted in lipid coating to the tip of the micro-pipette (FIG. 1a). On touching a loosely adherent neutrophil (diameter=10 µm) with the lipid coated micro-pipette, the $DiIC_{18}(3)$ was transferred to the cell (FIG. 1b). Initially, $DiIC_{18}(3)$ fluorescence was strongest at the point of contact whereas later the fluorescence became more uniform with significant fluorescence at the opposite pole of the cell. This was consistent with the transfer of $DiIC_{18}(3)$ transfer from the lipid coated micropipette to the cell membrane by direct contact and the result of the formation of a lipid "bridge" between the micropipette and the plasma membrane of the cell.

Thus, in FIG. 1(a) the series of images show (i) the phase contrast view of a single neutrophil with the lipid coated micro-pipette before contact, (ii) the fluorescent image of DiI staining marking the site of lipid at the micro-pipette tip, and (iii) the superimposition of the fluorescence and phase contrast images. In FIG. 1(b) the series of images shows (i) contact between the micro-pipette and the neutrophil under phase contrast, (ii) the fluorescent image of DiI transfer to the neutrophil membrane immediately after contact where the fluorescence is brightest at the micro-pipette contact point and (iii) 2 mins later when the fluorescent is more uniformly distributed around the cell membrane.

(ii) Acqueous transfer

In order to determine whether an aqueous-filled lipid bridge formed on contact between the lipid-coated micropipette and the cell, lucifer yellow was loaded into the micro-pipette and used as a marker of aqueous phase transfer between the contents of the micro-pipette and the cell cytosol. Although "stab" injection by an untreated micropipette could transfer lucifer yellow to the cell, merely touching the cell with the micro-pipette failed to transfer any detectable lucifer yellow to the cell cytosol (FIG. 2).

However, coating the micro-pipette tip with lipid produced significant transfer of lucifer yellow to the cell (FIG. 2). This was therefore also consistent with the formation of an aqueous-filled lipid bridge from the micro-pipette tip to the cell cytosol. This formed the basis for introducing material into the neutrophil cytosol without penetration of the cell and this technique was thus characterised to determine whether it occurred without excessive cell damage.

Thus, in FIG. 2 the series of images show (i) the uncoated micro-pipette touching a neutrophil and the consequent lack of transfer of fluorescent. Lucifer yellow seen in (ii) the fluorescent image. In image (iii) the procedure was repeated after coating the micro-pipette tip with lipid showing (iv) transfer of dye to the neutrophil and (v) under fluoresce microscopy for comparison with image (ii).

(iii) Cellular "damage"

It was important to determine whether the "SLAM" procedure was significantly less harmful to the cells than stab injection. This could be assessed by the use of trypan blue. By the addition of trypan blue to the incubation medium, gross damage to the cell was detectable as the dye accumulation within the cell. With "stab" injection, few (less than 5%) neutrophils survive the "stab" without becoming trypan blue positive and were thus discounted as non-viable. In contrast, under optimal conditions, the "SLAM" procedure produced very good survival rates, with trypan blue exclusion after "SLAM" being close to 100%. A critical factor in determining the survival of the neutrophil after "SLAM" was the pressure exerted by the micro-pipette within the cell. This could be monitored by the amount of material injected in unit time. FIG. 3 shows a demonstration experiment in which three neutrophils have been SLAM-injected with different pressures to illustrate the problem of using retention of lucifer yellow alone as a criterion for successful micro-injection. The middle cell was SLAM-injected at a pressure which was sufficient to completely rupture the cell, as seen in both the final fluorescent and bright field images. The upper cell was SLAM-injected at a pressure (10 mbar) which injected an appropriate amount into the cell (approximately 1% of its volume), causing no increase in permeability to trypan blue which was excluded from the cell. However, the lower cell was SLAM-injected with an intermediate pressure which did not rupture the cell and permitted the retention of micro-injected lucifer yellow. However, it is clear from the inclusion of trypan blue that cellular damage had occurred and that this pressure was too high.

Thus, in FIG. 3 the series of images show (i) the last of first of neutrophils micro-injected by the SLAM procedure at various injection pressures approximately as follows: upper cell, 10 mbar, lower cell, 50 mbar and middle cell 100 mbar. Images (ii) and (iii) show the corresponding loading of Lucifer yellow and trypan blue respectively after all three were micro-injected. As seen in image (ii) the middle cell was lysed by excessive pressure and did not retained Lucifer yellow, whereas the lower cell retainer Lucifer yellow but also failed to exclude trypan blue. The upper cell represents an optimal micro-injection in which Lucifer yellow was retained but trypan blue was excluded.

(iv) Characterisation of lipid-assisted micro-injection

Whilst the applicant is not to be bound thereby, the following is a proposal for characterisation of the lipid-assisted micro-injection.

Figure 5:
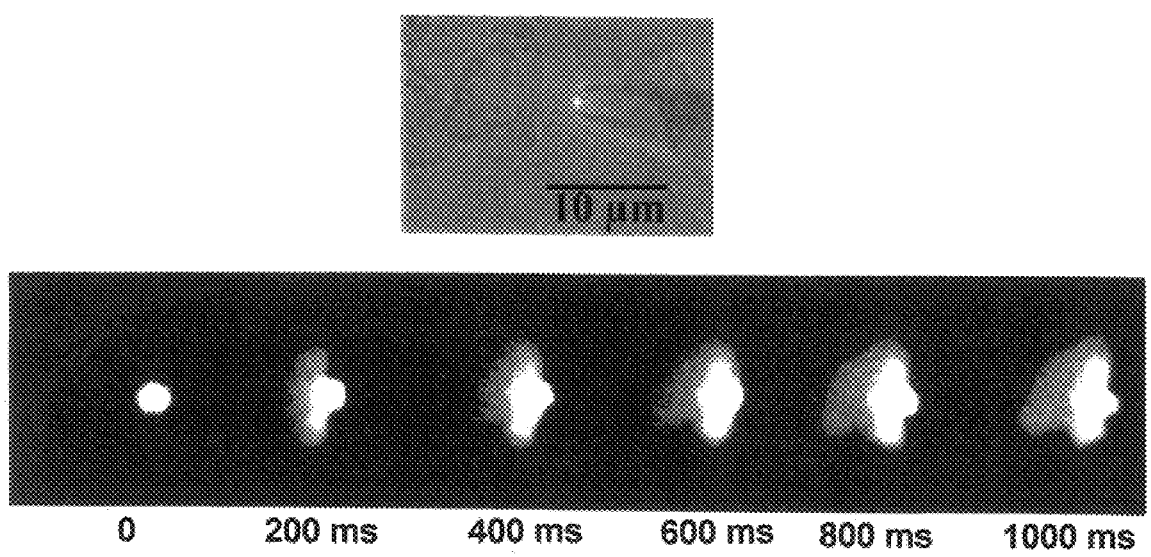
FIG. 5 shows images illustrating the entry of material into cytosol by diffusion.

Under the appropriately low pressure for micro-injection (10 mbar), there was an apparent increase in cell volume, as determined by cell diameter or change in cell shape. In order to gain an insight into the mechanism by which the aqueous material entered the cell, the time course of the increase in cell fluorescence was determined. There were two characteristics of the entry of aqueous material. The first was that micro-injection did not occur immediately on contact between the micro-pipette and the cell (FIG. 4). This was often less than 1 second, but in some cases was several seconds. This may be consistent with the formation of a lipid bridge resulting from the fusion of the lipid at the micro-pipette tip and the cell membrane. The second was that a quasi-equilibrium was formed within about 20 seconds of contact with the rate of rise of fluorescence within the cell being approximately constant between different cells, with a $t_{1/2}$ being about 10 seconds. One possibility for the quasi-equilibrium was that further material was not injected at the initial rate because the pressure within the micro-pipette and the internal pressure within the cell was approximately equal. From frame by frame imaging of the first second of the "SLAM" procedure, a clear wave of fluorescent material entering the cell was observed (FIG. 5). It was difficult to distinguish whether this wave resulted from diffusion of material from the micro-pipette or by low pressure injection, but the kinetics could be described by diffusion. The estimated diffusion constant for lucifer yellow with the neutrophil was thus D=100 $\mu m^2$/sec (simply travelling about 10 $\mu m$ in about 1 sec). As this value is similar to that expected for a small molecule in cytosol (eg $D_{const}$ for $IP_3$=283 $\mu m$/sec), this suggested that the entry of material in the first second may be by diffusion.

Thus, in FIG. 4, the graph shows the fluorescent intensity of Lucifer yellow within the neutrophil (shown in the insert) during the SLAM process. Contact between the lipid coated micro-pipette containing Lucifer yellow and the cell is marked on the trace by an arrow. The series of images below the same cell during the first 25 sec after contact between a micro-pipette. The position of the micro-pipette tip was visualised with DiI. In FIG. 5 the lower series of images show the fluorescent distribution of Lucifer yellow within the neutrophil shown upper panel after contact with the micro-pipette. The images for the first second as shown.

Using the above approach, the applicants have demonstrated the successful micro-injection of neutrophils both loosely adherent (about 10 $\mu m$ diameter) and thinly spread (about 1 $\mu m$ thick) which remain viable and chemotactic.

Further Information on Production of Lipid-Coated Micro-Pipettes

Figure 6:
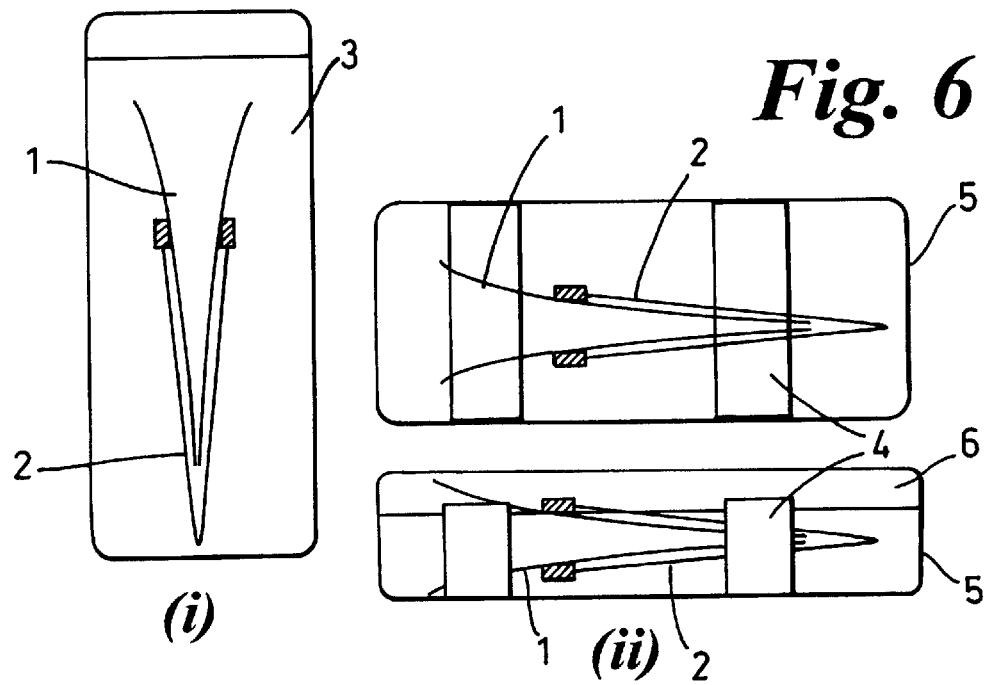
FIG. 6(ii) shows a plan and side view of an alternative packaging.

The production of micro-pipettes which are pre-coated with lipid can be mass produced by bringing the tip of the micro-pipette into contact with lipid dissolved in a volatile solvent. This can be achieved by simple immersion of the micro-pipettes in solutions of the lipid or by passage of the micro-pipettes through an aerosol spray of the lipid solution. Evaporation of the solvent leaves the tip of the micro-pipette appropriately coated with lipid. It is important the conditions under which the lipid-coated micro-pipettes are packaged maximise preservation of the lipid in its original molecular form. Thus water and water vapour should be excluded by enclosure of the lipid-coated micro-pipette in an outer air-tight sheath and packaging. This could be enhanced by inclusion of silica gel or similar agent which absorbs water vapour in the packaging. The outer packaging should also be flushed with an inert gas such as nitrogen before sealing to minimise oxidation of the lipid. The packaging and protective sheath would be easily removed by the user before use. The packaging is shown in FIGS. 6(i) and (ii). The micro-pipette or rod 1 in FIG. 6(i) is positioned within a plastic sheath 2 and then packaged within a bag 3 which is sealed. The bag 3 is designed to exclude air, moisture and light and is filled with an inert gas or is vacuum sealed. Alternatively, in FIG. 6(ii) the pipette or rod 1 is held on supports 4 within a solid box 5 having a lid 6. The sheath 2 may or may not be present, as required. The box 5 excludes air, moisture and light and is filled with an inert gas or is vacuum sealed. For use, the substance to be micro-injected would be placed into the micro-pipette from the rear (nonlipid-coated end). The bi-molecular lipid layer would form on the micro-pipette as it was immersed in aqueous liquid surrounding the cell to be micro-injected. High pressure (approx. 1000–3000 millibar) would then transiently applied (0.1–2 sec) to the micro-pipette to break the lipid seal and force the contents to the tip of the micro-pipette. On cessation of the high pressure pulse, the lipid at the tip reforms and the micro-pipette is ready for use in lipid-assisted micro-injection techniques.

An alternative to lipid pre-coating which eliminates the problem of lipid oxidation and destruction, is to provide the lipid as solution in a volatile solvent in an air-tight container. The container would be designed to permit the micro-pipette to be inserted into the solvent and thus be coated with lipid as, previously described. In order to minimise the possibility of damaging the delicate tip of the micro-pipette, the micro-pipette should be housed in an outer sheath which has an aperture at the base and rim. This will allow the entry of the solvent into the sheath and coat the micro-pipette with lipid without the possibility of damaging the inner glass micro-pipette tip. The sheath would then be removed before use to expose the lipid-coated micro-pipette. This allows for preparation in situ of the pipette for subsequent micro-injection techniques.

Figure 7:
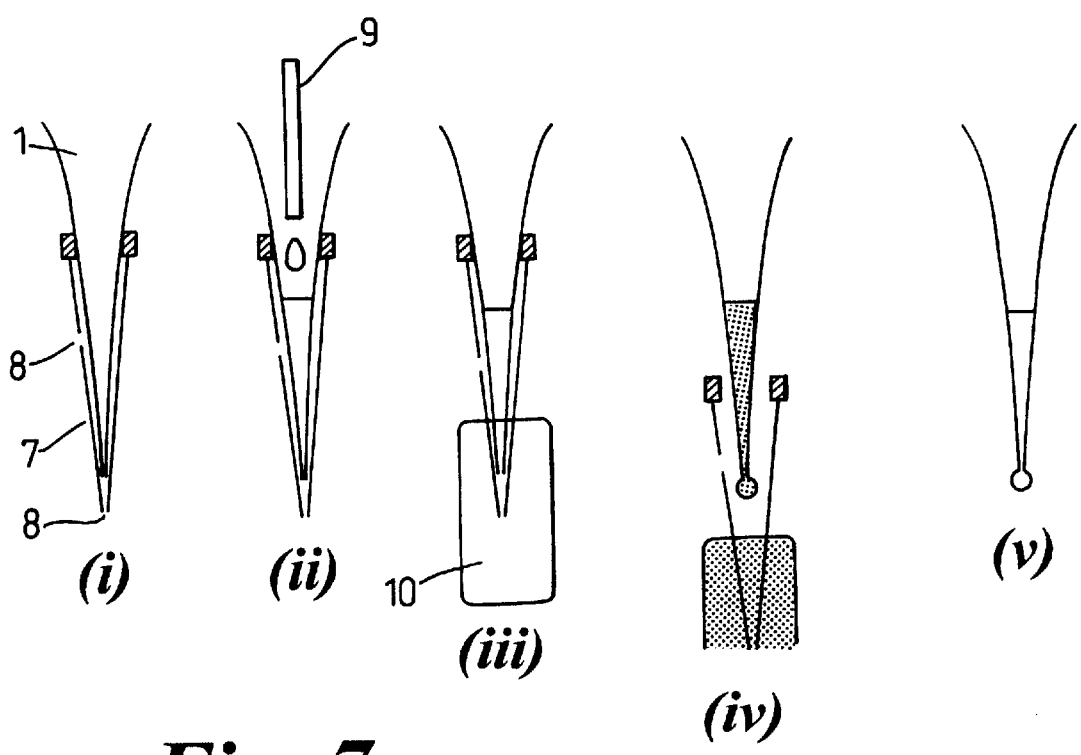
FIGS. 7(i)–7(v) show a method for lipid-coating within a protective sheath.

This is shown in FIGS. 7(i) to (v). A glass pipette or rod 1 is positioned in a plastic sheath 7 which has apertures 8 therein. The pipette is filled from filling device 9 with the required aqueous solution. The tip of sheath 7 is immersed in the lipid solution 10. The apertures 8 allow the lipid solution 10 to enter and contact the glass. The sheath 7 is removed leaving the pipette or rod 1 coated with lipid and ready for use.

We claim:

1. A method for introducing an agent into the cytosol and/or plasma membrane of a cell, comprising the steps of:
    (a) coating at least a portion of a tip of a transferring apparatus with a lipid;
    (b) bringing the lipid-coated tip of the transferring apparatus into contact with the cell; and
    (c) transferring at least some of the contents of the transferring apparatus into the cytosol and/or plasma membrane of the cell without entering the cytoplasm.

2. A method according to claim 1, wherein the transferring apparatus is a pipette or rod.

3. A method according to claim 1, wherein the contents of the transferring apparatus are transferred under pressure, which pressure is low enough to prevent damage to the cell.

4. A method according to claim 3, wherein the pressure is between 5 and 40 mbar.

5. A method according to claim 1, wherein the cell is a living cell which remains living after transferring at least some of the contents of the transferring apparatus into the cytosol and/or plasma membrane of the cell.

6. A method according to claim 1, wherein the cell is a small mammalian cell.

7. A method according to claim 1, wherein the spherical diameter of the cell is 2 to 15 $\mu$m.

8. A method according to claim 1, wherein the cell is of a flat form of 1 to 3 $\mu$m thickness.

9. A method according to claim 1, wherein the cell is a human neutrophil cell, having a thickness of 1–3 $\mu$m.

10. A method according to claim 1, wherein transfer of the lipid takes place between the transferring apparatus and the cytosol and/or plasma membrane of the cell.

11. A method according to claim 1, wherein the contents of the transferring apparatus are in the form of an aqueous solution.

12. A method according to claim 1, further comprising the step of swelling the lipid to form a lipid-coating or bi-molecular layer prior to bringing the tip into contact with the cell.

13. A method according to claim 1, wherein the lipid comprises phosphatidylcholine-oleyl-palmitoyl (PCOP).

14. A transferring apparatus for introducing an agent into the cytosol and/or plasma membrane of a cell, comprising a lipid-coated tip capable of transferring at least some of the contents of the transferring apparatus into the cell without entering the cytoplasm.

15. A lipid-coated tip for use in the transferring apparatus according to claim 14.

16. A kit for introducing an agent into a cell, the kit comprising an agent and a transferring apparatus for introducing the agent into the cytosol and/or plasma membrane of a cell, wherein the apparatus comprises a lipid-coated tip capable of transferring at least some of the contents of the apparatus into the cytosol and/or plasma membrane of the cell without entering the cytoplasm.

17. A method of introducing a transfection agent into a cell, the method comprising the steps of:
    (a) coating at least a portion of a tip of a transferring apparatus with a lipid;
    (b) bringing the lipid-coated tip of the transferring apparatus into contact with the cell; and
    (c) transferring at least some of the contents of the transferring apparatus which comprise the transfection agent, into the cell.

18. A method of coating a tip of a transferring apparatus with a lipid, comprising applying a lipid solution to the tip of the transferring apparatus and evaporating the solvent from the lipid solution.

19. A method according to claim 18, wherein the lipid solution is provided in an air-tight and light-tight container.

20. A method according to claim 18, further comprising the step of loading the transferring apparatus with an aqueous solution prior to applying the lipid solution.

21. A method according to claim 18, further comprising the step of placing the transferring apparatus in an aqueous solution such that the dried lipid swells to form a lipid-coating or bi-molecular layer.

22. A method of preparing a lipid-coated tip of a transferring apparatus, comprising:
    (a) positioning a tip of a transferring apparatus in a sheath having an aperture therein;
    (b) immersing the tip in a lipid in a solvent thereby allowing the solvent to pass through the aperture; and
    (c) evaporating the solvent.

23. A method according to claim 22, wherein an aperture is positioned in a base and a side wall of the sheath.

24. A method according to claim 22, further comprising the step of removing the sheath.

25. A method according to claim 22, further comprising the step of filling the transferring apparatus prior to immersion in, the solvent.

* * * * *